(12) United States Patent
Raillard et al.

(10) Patent No.: US 9,533,941 B2
(45) Date of Patent: *Jan. 3, 2017

(54) METHODS OF SYNTHESIZING A LEVODOPA ESTER PRODRUG

(71) Applicant: XENOPORT, INC., Santa Clara, CA (US)

(72) Inventors: Stephen P. Raillard, Mountain View, CA (US); Adam Mann, Sunnyvale, CA (US); Suresh K. Manthati, Sunnyvale, CA (US); Randall A. Scheuerman, Santa Clara, CA (US); Tono Estrada, Santa Clara, CA (US); Mark Q. Nguyen, Santa Clara, CA (US); Cindy X. Zhou, Santa Clara, CA (US)

(73) Assignee: XENOPORT, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/043,278

(22) Filed: Feb. 12, 2016

(65) Prior Publication Data

US 2016/0176804 A1 Jun. 23, 2016

Related U.S. Application Data

(63) Continuation of application No. 12/581,808, filed on Oct. 19, 2009, now Pat. No. 9,290,445.

(60) Provisional application No. 61/106,930, filed on Oct. 20, 2008.

(51) Int. Cl.
$C07C\ 227/20$ (2006.01)
$C07C\ 269/04$ (2006.01)
$C07C\ 67/20$ (2006.01)
$C07C\ 269/06$ (2006.01)

(52) U.S. Cl.
CPC ............ $C07C\ 227/20$ (2013.01); $C07C\ 67/20$ (2013.01); $C07C\ 269/04$ (2013.01); $C07C\ 269/06$ (2013.01)

(58) Field of Classification Search
None
See application file for complete search history.

*Primary Examiner* — Sudhakar Katakam
*Assistant Examiner* — Jennifer C Sawyer
(74) *Attorney, Agent, or Firm* — King & Spalding LLP

(57) ABSTRACT

Methods of synthesizing a levodopa ester prodrug, salts thereof, and synthetic intermediates thereof are disclosed.

10 Claims, 1 Drawing Sheet

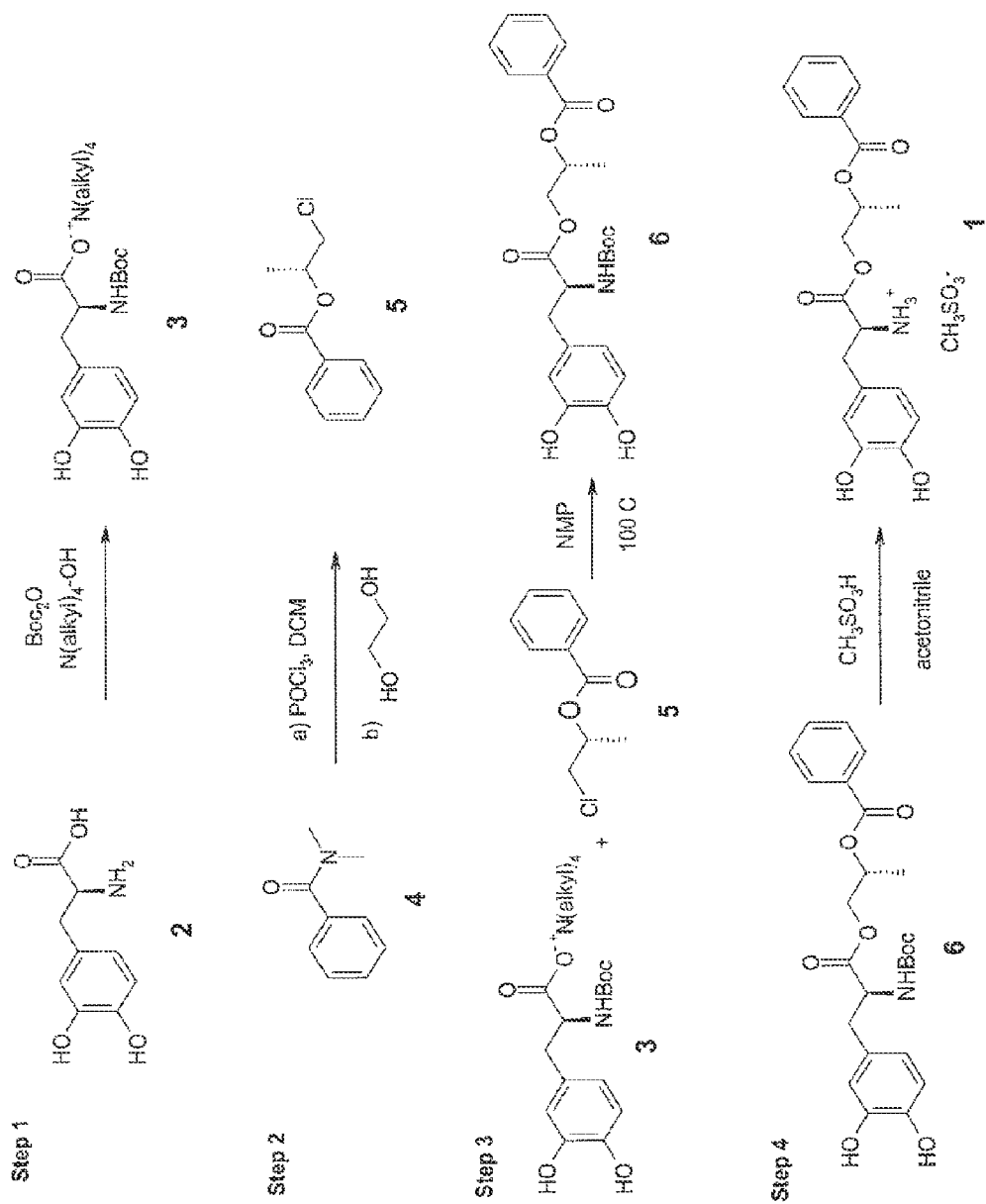

METHODS OF SYNTHESIZING A LEVODOPA ESTER PRODRUG

This application is a continuation of U.S. application Ser. No. 12/581,808 filed on Oct. 19, 2009, now allowed, which claims the benefit under 35 U.S.C. §119(e) of U.S. Provisional Application No. 61/106,930, filed on Oct. 20, 2008, each of which is incorporated by reference in its entirety.

The present disclosure relates to methods of synthesizing a levodopa ester prodrug and synthetic intermediates thereof.

Parkinson's disease is a disabling, progressive illness that affects one in 1,000 people and generally occurs in people over the age of 50 years. Patients with Parkinson's disease have a deficiency of the neurotransmitter dopamine in the brain as a result of nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

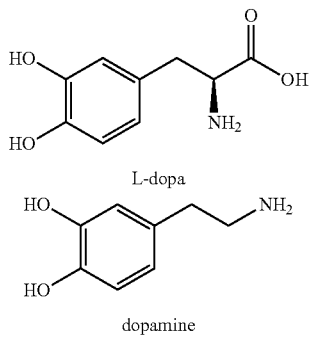

Following oral administration, levodopa is rapidly absorbed via an amino acid transporter present in the upper small intestine. Due to the narrow distribution of this transporter system, the window available for levodopa absorption is limited and the extent of absorption can depend on the rate at which the drug passes through the upper gastrointestinal tract.

Intestinal metabolism of levodopa is the major source of first pass loss of the drug. Approximately 35% of an administered dose of levodopa reaches the systemic circulation as intact levodopa after oral administration in patients (Sasahara, *J. Pharm. Sci* 1990, 69, 261). Once absorbed, levodopa is rapidly metabolized to dopamine by L-aromatic amino acid decarboxylase (AADC) enzymes in the peripheral tissues (e.g., intestines and liver). For this reason, levodopa is normally co-administered with a decarboxylase enzyme inhibitor such as carbidopa or benserazide. When administered with carbidopa, the plasma concentration of intact levodopa increases and thus more levodopa becomes available to be transported into the central nervous system where it is converted to dopamine. Carbidopa and benserazide do not cross the blood-brain barrier to a significant extent and therefore do not inhibit the required conversion of levodopa to dopamine in the brain.

The use of prodrugs of levodopa to improve the pharmacokinetics of levodopa has been proposed. Levodopa prodrugs designed to be absorbed in both the small and large intestines and methods of synthesizing such prodrugs have been described in Xiang et al., U.S. Pat. No. 7,323,585, U.S. Patent Application Publication No. 2008/0103200, U.S. Pat. No. 7,342,131, U.S. Pat. No. 7,534,813, U.S. Pat. No. 7,563,821, U.S. Patent Application Publication No. 2008/0171789, and U.S. Patent Application Publication No. 2008/0214663, each of which is incorporated by reference in its entirety. These levodopa prodrugs can achieve an oral bioavailability of levodopa that is at least two times greater than the oral bioavailability of levodopa when orally administered on an equivalent molar basis. More specifically, Xiang et al., U.S. Pat. No. 7,342,131 disclose the compound (2R)-2-phenylcarbonyloxypropyl (2S)-2-amino-3-(3,4-dihydroxyphenyl)propanoate hydrochloride in an amorphous or crystalline form (see Example 8 of Xiang et al.), and Xiang et al., U.S. Pat. No. 7,563,821 discloses the (2R)-2-phenylcarbonyloxypropyl (2S)-2-amino-3-(3,4-dihydroxyphenyl)propanoate, methanesulfonate salt. The prodrugs described by Xiang et al. can be efficaciously incorporated into sustained release formulations to provide sustained systemic exposure to levodopa upon oral administration to a patient.

Xiang et al., U.S. Pat. No. 7,144,877 describe the synthesis of acyloxyalkyl prodrugs of L-dopa by reacting Boc-protected L-dopa with a halide in the presence of a base such as an alkali metal bicarbonate or carbonate followed by hydrolysis of the Boc protecting group under acidic conditions to provide the corresponding acyloxyalkyl L-dopa prodrug. Xiang et al., U.S. Pat. No. 7,144,877 also describe an alternate route of synthesizing L-dopa prodrugs via coupling of Boc-protected L-dopa with an alcohol intermediate under standard couple conditions followed by removal of the Boc protecting group. Xiang et al., U.S. Patent Application Publication No. 2008/0171789 and U.S. Patent Application Publication No. 2008/0214663 disclose the synthesis of acyloxyalkyl L-dopa prodrugs from diols, from 2-hydroxyethyl halides, or from ethylene dihalides.

Alternative methods of synthesizing (2R)-2-phenylcarbonyloxypropyl (2S)-2-amino-3-(3,4-dihydroxyphenyl)propanoate, methanesulfonate and other pharmaceutically acceptable salts of (2R)-2-phenylcarbonyloxypropyl (2S)-2-amino-3-(3,4-dihydroxyphenyl)propanoate that are synthetically robust and provide the desired levodopa prodrugs with high yield and reasonable purity are disclosed.

In a first aspect, methods of synthesizing (2R)-2-phenylcarbonyloxypropyl (2S)-2-amino-3-(3,4-dihydroxyphenyl) propanoate are disclosed comprising reacting 3-(3,4-dihydroxyphenyl)-(2S)-[(tert-butoxy)carbonylamino]propanoate tetraalkylammonium salt with (1R)-2-halogen-isopropyl benzoate in a first solvent to provide (2R)-2-phenylcarbonyloxypropyl (2S)-3-(3,4-dihydroxyphenyl)-2-[(tert-butoxy)carbonylamino]propanoate.

In a second aspect, methods of synthesizing 3-(3,4-dihydroxyphenyl)-(2S)-[(tert-butoxy)carbonylamino]propanoate tetraalkylammonium salt are disclosed comprising reacting (2S)-2-amino-3-(3,4-dihydroxyphenyl)propanoic acid with di-tert-butyl dicarbonate and tetraalkylammonium hydroxide in a mixture of alcohol and water at a temperature ranging from about 20° C. to about 60° C. in an inert atmosphere to provide 3-(3,4-dihydroxyphenyl)-(2S)-[(tert-butoxy)carbonylamino]propanoate tetraalkylammonium salt.

In a third aspect, the compound 3-(3,4-dihydroxyphenyl)-(2S)-[(tert-butoxy)carbonylamino]propanoate tetraalkylammonium salt is disclosed.

BRIEF DESCRIPTION OF THE DRAWINGS

Those skilled in the art will understand that the drawings described herein are for illustration purposes only. The drawings are not intended to limit the scope of the present disclosure.

FIG. 1 shows steps in the synthesis of (2R)-2-phenylcarbonyloxypropyl (2S)-2-amino-3-(3,4-dihydroxyphenyl)propanoate, methanesulfonate and synthetic intermediates wherein X is halogen.

Reference is now made in detail to certain embodiments of compounds, compositions, and methods. The disclosed embodiments are not intended to be limiting of the claims. To the contrary, the claims are intended to cover all alternatives, modifications, and equivalents.

Methods provided by the present disclosure include methods of synthesizing (2R)-2-phenylcarbonyloxypropyl (2S)-2-amino-3-(3,4-dihydroxyphenyl)propanoate, methanesulfonate 1 (also referred to (2R)-2-phenylcarbonyloxypropyl (2S)-2-amino-3-(3,4-dihydroxyphenyl)propanoate mesylate);

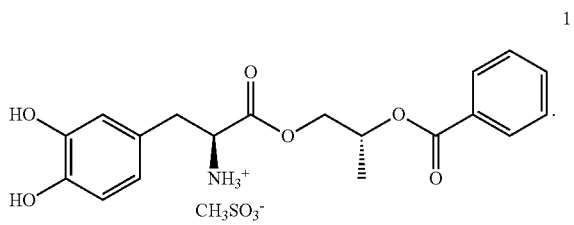

and other pharmaceutically acceptable salts of (2R)-2-phenylcarbonyloxypropyl (2S)-2-amino-3-(3,4-dihydroxyphenyl)propanoate.

In certain embodiments methods of synthesizing (2R)-2-phenylcarbonyloxypropyl (2S)-2-amino-3-(3,4-dihydroxyphenyl)propanoate are disclosed comprising reacting 3-(3,4-dihydroxyphenyl)-(2S)-[(tert-butoxy)carbonylamino]propanoate tetraalkylammonium salt with (1R)-2-halogen-isopropyl benzoate in a first solvent to provide (2R)-2-phenylcarbonyloxypropyl (2S)-3-(3,4-dihydroxyphenyl)-2-[(tert-butoxy)carbonylamino]propanoate.

In certain embodiments, the tetraalkylammonium salt is chosen from the tetramethyl ammonium salt, the tetraethylammonium salt, the tetrapropylammonium salt, and the tetrabutylammonium salt. In certain embodiments, the tetraalkylammonium salt is the tetraethylammoniumm salt, and in certain embodiments is the tetrabutylammonium salt.

In certain embodiments, the first solvent is chosen from N-methyl-2-pyrrolidone, dimethyl formamide, dimethyl acetamide, dimethylsulfoxide, 1,4-dioxane, and a mixture of any of the foregoing.

In certain embodiments, (1R)-2-halogen-isopropyl benzoate is (1R)-2-chloro-isopropyl benzoate.

In certain embodiments, the first solvent is N-methyl-2-pyrrolidone.

In certain embodiments, reacting 3-(3,4-dihydroxyphenyl)-(2S)-[(tert-butoxy)carbonylamino]propanoate tetraalkylammonium salt with (1R)-2-chloro-isopropyl benzoate in a first solvent to provide (2R)-2-phenylcarbonyloxypropyl (2S)-3-(3,4-dihydroxyphenyl)-2-[(tert-butoxy)carbonylamino]propanoate is carried out at a temperature ranging from about 70° C. to about 80° C.

In certain embodiments, the method further comprises reacting (2R)-2-phenylcarbonyloxypropyl (2S)-3-(3,4-dihydroxyphenyl)-2-[(tert-butoxy)carbonylamino]propanoate with an acid in a second solvent to provide the corresponding (2R)-2-phenylcarbonyloxypropyl (2S)-2-amino-3-(3,4-dihydroxyphenyl)propanoate salt.

In certain embodiments, the method further comprises reacting (2R)-2-phenylcarbonyloxypropyl (2S)-3-(3,4-dihydroxyphenyl)-2-[(tert-butoxy)carbonylamino]propanoate with methanesulfonic acid in a second solvent to provide (2R)-2-phenylcarbonyloxypropyl (2S)-2-amino-3-(3,4-dihydroxyphenyl)propanoate, methanesulfonate.

In certain embodiments, the second solvent is chosen from acetonitrile, acetone, ethyl acetate, toluene, isopropanol, dichloromethane, and a mixture of any of the foregoing.

In certain embodiments the second solvent is chosen from acetonitrile and dichlormethane. In certain embodiments, the second solvent is acetonitrile In certain embodiments, reacting (2R)-2-phenylcarbonyloxypropyl (2S)-3-(3,4-dihydroxyphenyl)-2-[(tert-butoxy)carbonylamino]propanoate with methanesulfonic acid in a second solvent to provide (2R)-2-phenylcarbonyloxypropyl (2S)-2-amino-3-(3,4-dihydroxyphenyl)propanoate, methanesulfonate is carried out at a temperature ranging from about 30° C. to about 50° C.

In certain embodiments, the method further comprises cooling the second solvent to form crystalline (2R)-2-phenylcarbonyloxypropyl (2S)-2-amino-3-(3,4-dihydroxyphenyl)propanoate, methanesulfonate.

In certain embodiments, the method further comprises seeding the cooled second solvent with crystalline (2R)-2-phenylcarbonyloxypropyl (2S)-2-amino-3-(3,4-dihydroxyphenyl)propanoate, methanesulfonate.

In certain embodiments, the method further comprises recrystallizing (2R)-2-phenylcarbonyloxypropyl (2S)-2-amino-3-(3,4-dihydroxyphenyl)propanoate, methanesulfonate.

In certain embodiments, recrystallizing (2R)-2-phenylcarbonyloxypropyl (2S)-2-amino-3-(3,4-dihydroxyphenyl)propanoate, methanesulfonate comprises dissolving (2R)-2-phenylcarbonyloxypropyl (2S)-2-amino-3-(3,4-dihydroxyphenyl)propanoate, methanesulfonate in a third solvent; and cooling the third solvent to form crystalline (2R)-2-phenylcarbonyloxypropyl (2S)-2-amino-3-(3,4-dihydroxyphenyl)propanoate, methanesulfonate.

In certain embodiments, the third solvent is chosen from acetonitrile, acetone, ethyl acetate, water, and a mixture of any of the foregoing.

In certain embodiments, the third solvent is chosen from acetonitrile and a mixture of acetonitrile and water.

In certain embodiments, (1R)-2-halogen-isopropyl benzoate is prepared comprising reacting N,N-dimethylbenzamide with phosphoryl halogen in a fourth solvent to provide dimethylbenzamide Vilsmeier salt; and reacting dimethylbenzamide Vilsmeier salt with (2R)-propane-1,2-diol to provide (1R)-2-halogen-isopropyl benzoate.

In certain embodiments, phosphoryl halogen is phosphoryl chloride and (1R)-2-halogen-isopropyl benzoate is (1R)-2-chloro-isopropyl benzoate.

In certain embodiments wherein phosphoryl halogen is phosphoryl chloride and (1R)-2-halogen-isopropyl benzoate is (1R)-2-chloro-isopropyl benzoate, reacting N,N-dimethylbenzamide with phosphoryl halogen to provide dimethylbenzamide Vilsmeier salt is carried out at a temperature ranging from about 70° C. to about 95° C.

In certain embodiments, the fourth solvent is dichloromethane.

In certain embodiments, wherein phosphoryl halogen is phosphoryl chloride and (1R)-2-halogen-isopropyl benzoate is (1R)-2-chloro-isopropyl benzoate reacting dimethylbenzamide Vilsmeier salt with (2R)-propane-1,2-diol to provide (1R)-2-chloro-isopropyl benzoate is carried out at a temperature ranging from about 0° C. to about 10° C.

In certain embodiments, 3-(3,4-dihydroxyphenyl)-(2S)-[(tert-butoxy)carbonylamino]propanoate tetraalkylammonium salt is prepared comprising reacting (2S)-2-amino-3-(3,4-dihydroxyphenyl)propanoic acid with di-tert-butyl dicarbonate and tetraalkylammonium hydroxide to provide 3-(3,4-dihydroxyphenyl)-(2S)-[(tert-butoxy)carbonylamino]propanoate tetraalkylammonium salt.

In certain embodiments, reacting (2S)-2-amino-3-(3,4-dihydroxyphenyl)propanoic acid with di-tert-butyl dicarbonate and tetraalkylammonium hydroxide to provide 3-(3,4-dihydroxyphenyl)-(2S)-[(tert-butoxy)carbonylamino]propanoate tetraalkylammonium salt is carried out in a mixture of an alcohol and water.

In certain embodiments, the mixture of an alcohol and water comprises from about 0%-b.v. to about 4%-b.v. water.

In certain embodiments, the alcohol is chosen from methanol, ethanol, isopropanol, and a mixture of any of the foregoing.

In certain embodiments, reacting (2S)-2-amino-3-(3,4-dihydroxyphenyl)propanoic acid with di-tert-butyl dicarbonate to provide 3-(3,4-dihydroxyphenyl)-(2S)-[(tert-butoxy)carbonylamino]propanoate tetraalkylammonium salt is carried out at a temperature ranging from about 30° C. to about 50° C.

Steps in the synthesis of (2R)-2-phenylcarbonyloxypropyl (2S)-2-amino-3-(3,4-dihydroxyphenyl)propanoate methanesulfonate 1 and synthetic intermediates are shown in FIG. 1.

In a first reaction step, Boc-L-dopa tetraalkylammonium salt 3 (3-(3,4-dihydroxyphenyl-(2S)-[(tert-butoxy)carbonylamino]propanoate tetraalkyl ammonium salt) can be prepared by reacting L-dopa 2 with di-tert-butyl dicarbonate (Boc-anhydride, $Boc_2O$) and tetraalkylammonium hydroxide in an alcohol/water mixture at a temperature ranging from about 20° C. to about 60° C. in an inert atmosphere. The amount of water in the alcohol/water mixture can range from about 0%-b.v. to about 5%-b.v., from about 1%-b.v. to about 4%-b.v., from about 1%-b.v. to about 3%-b.v., and in certain embodiments, is about 2%-b.v. In certain embodiments the alcohol can be chosen from methanol, ethanol, isopropanol, and a mixture of any of the foregoing, and in certain embodiments, the alcohol is methanol. Alternatively, the reaction can be carried out in a dipolar aprotic solvent such as N-methyl-2-pyrrolione (NMP), dimethyl formamide (DMF), dimethylacetamide (DMA), dimethyl sulfoxide (DMSO), or a mixture of any of the foregoing. In certain embodiments the temperature of the reaction can range from about 30° C. to about 60° C., from about 35° C. to about 55° C., and in certain embodiments, at a temperature of about 40° C.

(1R)-2-Chloro-isopropyl benzoate 5 can be prepared by reacting N,N-dimethylbenzamide with a phosphoryl halogen such as phosphoryl chloride (phosphorous oxychloride II, $POCl_3$) in an organic solvent such as dichloromethane under an inert atmosphere to provide the (chlorophenylmethylene)dimethylamide chloride salt (Vilsmeier salt) intermediate, which can then be reacted with (R)-1,2-propanediol to provide (1R)-2-chloro-isopropyl benzoate 5. Formation of the iminium intermediate can be carried out at a temperature ranging from about 65° C. to about 105° C. from about 75° C. to about 95° C., and in certain embodiments, at a temperature of about 85° C. The diol coupling reaction can be carried out by adding the diol to the reaction mixture while maintaining the temperature from about 0° C. to about 10° C., after which the reaction mixture can be warmed to a temperature ranging from about 15° C. to about 35° C., and in certain embodiments, to about 25° C., and allowed to react until the Vilsmeier salt intermediate is consumed.

In a third step, 3-(3,4-dihydroxyphenyl)-(2S)-[(tert-butoxy)carbonylamino]propanoate tetraalkylammonium salt 3 can be reacted under an inert atmosphere with (1R)-2-chloro-isopropyl benzoate 5 to provide (2R)-2-phenylcarbonyloxypropyl (2S)-3-(3,4-dihydroxyphenyl)-2-[(tert-butoxy)carbonylamino]propanoate 6.

The reaction can be carried out in a dipolar aprotic solvent such as N-methyl-2-pyrrolione (NMP), dimethyl formamide (DMF), dimethylacetamide (DMA), dimethyl sulfoxide (DMSO), 1,4-dioxane, or a mixture of any of the foregoing. In certain embodiments, the solvent is N-methyl-2-pyrrolione (NMP). The temperature of the reaction can range from about 50° C. to about 120° C., from about 70° C. to about 80° C., and in certain embodiments, at a temperature of about 75° C.

In a fourth step, (2R)-2-phenylcarbonyloxypropyl (2S)-3-(3,4-dihydroxyphenyl)-2-[(tert-butoxy)carbonylamino]propanoate 6 can be reacted with methanesulfonic acid to provide (2R)-2-phenylcarbonyloxypropyl (2S)-2-amino-3-(3,4-dihydroxyphenyl)propanoate, methanesulfonate 1. The reaction can be carried out in a solvent chosen from isopropanol, acetonitrile, toluene, dichloromethane, and a mixture of any of the foregoing. In certain embodiments, the solvent is chosen from acetonitrile and dichloromethane. The reaction can be carried out at a temperature ranging from about 20° C. to about 60° C., from about 30° C. to about 50° C., and in certain embodiments, at a temperature of about 40° C. (2R)-2-Phenylcarbonyloxypropyl (2S)-2-amino-3-(3,4-dihydroxyphenyl)propanoate, methanesulfonate 1 can precipitate from the solution as a crystalline solid, i.e., crystalline (2R)-2-phenylcarbonyloxypropyl (2S)-2-amino-3-(3,4-dihydroxyphenyl)propanoate, methanesulfonate 1.

Using appropriate reaction conditions such as those described for the synthesis of (2R)-2-phenylcarbonyloxypropyl (2S)-2-amino-3-(3,4-dihydroxyphenyl)propanoate, methanesulfonate 1 in the fourth step, other salts of (2R)-2-phenylcarbonyloxypropyl (2S)-2-amino-3-(3,4-dihydroxyphenyl)propanoate can be prepared. For example, methanesulfonic acid can be replaced with a different acid and reacted using an appropriate solvent and at an appropriate temperature to provide the corresponding (2R)-2-phenylcarbonyloxypropyl (2S)-2-amino-3-(3,4-dihydroxyphenyl)propanoate salt. In certain embodiments, the acid is chosen from hydrochloric acid, sulfuric acid, phosphoric acid, methanesulfonic acid, ethanesulfonic acid, benzenesulfonic acid, and 4-toluenesulfonic acid, to produce the corresponding pharmaceutically acceptable salt of (2R)-2-phenylcarbonyloxypropyl (2S)-2-amino-3-(3,4-dihydroxyphenyl)propanoate.

"Pharmaceutically acceptable" refers to approved or approvable by a regulatory agency of the Federal or a state government or listed in the U.S. Pharmacopoeia or other generally recognized pharmacopoeia for use in animals, and more particularly in humans. Pharmaceutically acceptable salt refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt, and in certain embodiments, the sodium salt. In certain embodiments, a pharmaceutically acceptable salt is the methanesulfonic acid salt.

(2R)-2-Phenylcarbonyloxypropyl (2S)-2-amino-3-(3,4-dihydroxyphenyl)propanoate, methanesulfonate 1 can be recrystallized by first dissolving the compound in a solvent chosen from acetonitrile, isopropanol, toluene, water, and a mixture of any of the foregoing and a trace amount of water. In certain embodiments, the solvent is chosen from acetonitrile and a mixture of acetonitrile and water. The solution can then be filtered and then slowly cooled to precipitate crystalline (2R)-2-phenylcarbonyloxypropyl (2S)-2-amino-3-(3, 4-dihydroxyphenyl)propanoate, methanesulfonate 1. Using the methods disclosed herein, (2R)-2-phenylcarbonyloxypropyl (2S)-2-amino-3-(3,4-dihydroxyphenyl)propanoate, methanesulfonate 1 can be synthesized with an overall yield of about 20% to about 25%, and with purity greater than about 95% purity, greater than about 97% purity, and in certain embodiments, greater than about 98% purity.

(2R)-2-Phenylcarbonyloxypropyl (2S)-2-amino-3-(3,4-dihydroxyphenyl)propanoate methanesulfonate 1 may exist in several tautomeric forms. Accordingly, all possible tautomeric forms of (2R)-2-phenylcarbonyloxypropyl (2S)-2-amino-3-(3,4-dihydroxyphenyl)propanoate methanesulfonate are encompassed unless otherwise specified. All isotopically labeled forms of (2R)-2-phenylcarbonyloxypropyl (2S)-2-amino-3-(3,4-dihydroxyphenyl)propanoate methanesulfonate are also encompassed unless otherwise specified. Examples of isotopes that may be incorporated into (2R)-2-phenylcarbonyloxypropyl (2S)-2-amino-3-(3,4-dihydroxyphenyl)propanoate methanesulfonate include, but are not limited to, $^2$H, $^3$H, $^{11}$C, $^{13}$C, $^{14}$C, $^{15}$N, $^{18}$O, and $^{17}$O.

In certain embodiments, (2R)-2-phenylcarbonyloxypropyl (2S)-2-amino-3-(3,4-dihydroxyphenyl)propanoate methanesulfonate 1 is crystalline. In certain embodiments, an X-ray powder diffraction pattern of crystalline (2R)-2-phenylcarbonyloxypropyl (2S)-2-amino-3-(3,4-dihydroxyphenyl)propanoate methanesulfonate exhibits characteristic scattering angles °2θ at least at 4.7±0.2°, 5.0±0.2°, 8.5±0.2°, 9.6±0.2°, 13.6±0.2°, 15.0±0.2°, 17.0±0.2°, 17.4±0.2°, 17.7±0.2°, 19.1±0.2°, 19.5±0.2°, 20.0±0.2°, 20.4±0.2°, 21.1±0.2°, 22.3±0.2°, 22.9±0.2°, 23.1±0.2°, 23.3±0.2°, 24.3±0.2°, 25.0±0.2°, 25.3±0.2°, 25.7±0.2°, 25.8±0.2°, 26.9±0.2°, 27.3±0.2°, 28.2±0.2°, 30.1±0.2°, 30.5±0.2°, 32.0±0.2°, 33.8±0.2°, 34.3±0.2°, 37.6±0.2°, and 38.4±0.2° using Cu-Kα radiation. In certain embodiments, an X-ray powder diffraction pattern of crystalline (2R)-2-phenylcarbonyloxypropyl (2S)-2-amino-3-(3,4-dihydroxyphenyl)propanoate methanesulfonate exhibits characteristic scattering angles °2θ at least at 5.0±0.2°, 8.5±0.2°, 13.6±0.2°, 15.0±0.2°, 17.0±0.2°, 17.7±0.2°, 20.4±0.2°, 21.1±0.2°, 25.0±0.2°, 25.8±0.2°, 28.2±0.2°, 30.1±0.2°, and 37.6±0.2° using Cu-Kα radiation. One skilled in the art will recognize that slight variations in the observed °2θ diffraction angles can be expected based on, for example, the specific diffractometer employed, the analyst, and the sample preparation technique. Greater variation can be expected for the relative peak intensities. Comparison of diffraction patterns can be based primarily on observed °2θ diffraction angles with lesser importance attributed to relative peak intensities.

In certain embodiments, crystalline (2R)-2-phenylcarbonyloxypropyl (2S)-2-amino-3-(3,4-dihydroxyphenyl)propanoate methanesulfonate exhibits a melting point ranging from about 157° C. to about 162° C.

In certain embodiments, crystalline (2R)-2-phenylcarbonyloxypropyl (2S)-2-amino-3-(3,4-dihydroxyphenyl)propanoate methanesulfonate is characterized by a differential scanning calorimetry (DSC) thermogram having an endothermic peak at about 164.5° C., and in certain embodiments at about 164.5±2.5° C.

In certain embodiments, crystalline (2R)-2-phenylcarbonyloxypropyl (2S)-2-amino-3-(3,4-dihydroxyphenyl)propanoate methanesulfonate is stable, e.g., does not absorb moisture and/or convert to another isomorphic form under pharmaceutical processing and/or storage conditions.

Levodopa prodrugs are precursors of dopamine. Thus, (2R)-2-phenylcarbonyloxypropyl (2S)-2-amino-3-(3,4-dihydroxyphenyl)propanoate methanesulfonate synthesized using methods provided by the present disclosure may be administered to a patient suffering from any disease or disorder for which the parent drug, levodopa, is known or hereafter determined to be therapeutically effective. (2R)-2-Phenylcarbonyloxypropyl (2S)-2-amino-3-(3,4-dihydroxyphenyl)propanoate methanesulfonate may be administered to a patient, such as a human, to treat a disease or disorder such as Parkinson's disease. The methods comprise administering to a patient in need of such treatment a therapeutically effective amount of (2R)-2-phenylcarbonyloxypropyl (2S)-2-amino-3-(3,4-dihydroxyphenyl)propanoate methanesulfonate. In therapeutic methods provided by the present disclosure, a therapeutically effective amount of (2R)-2-phenylcarbonyloxypropyl (2S)-2-amino-3-(3,4-dihydroxyphenyl)propanoate methanesulfonate may be administered to a patient suffering from a disease such as Parkinson's disease, depression, attention deficit disorder, schizophrenia, manic depression, a cognitive impairment disorder, restless legs syndrome, a periodic limb movement disorder, tardive dyskinesia, Huntington's disease, Tourette's syndrome, hypertension, an addictive disorder, congestive heart failure, or excessive daytime sleepiness.

As used herein, the abbreviation "b.v." or "bv" means "by volume". Particularly, when referencing a mixture of more than one fluids, the term % b.v. reflects the percentage of one fluid in the total volume. As a non-limiting example a mixture of methanol and water that is 10% b.v. water comprises 10 units of water and 90 units of methanol.

EXAMPLES

The following examples describe in detail the preparation of (2R)-2-phenylcarbonyloxypropyl (2S)-2-amino-3-(3,4-dihydroxyphenyl)propanoate, methanesulfonate and synthetic intermediates using methods disclosed herein. It will be apparent to those skilled in the art that many modifications, both to materials and methods, may be practiced without departing from the scope of the disclosure.

Example 1

Synthesis of (2R)-2-Phenylcarbonyloxypropyl (2S)-2-amino-3-(3,4-dihydroxyphenyl)propanoate, Methanesulfonate (1)

Step 1: Boc-L-Dopa tetrabutylammonium salt (3)

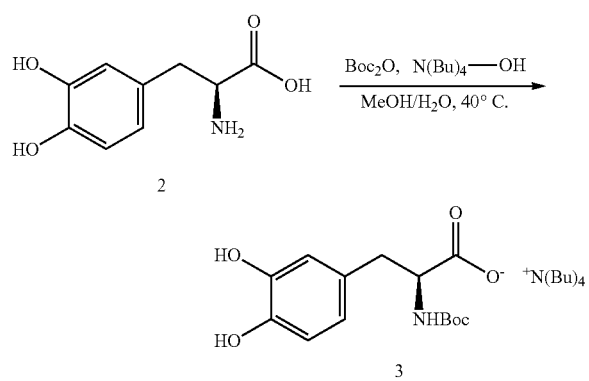

Step 2: (1R)-2-Chloro-isopropyl Benzoate (5)

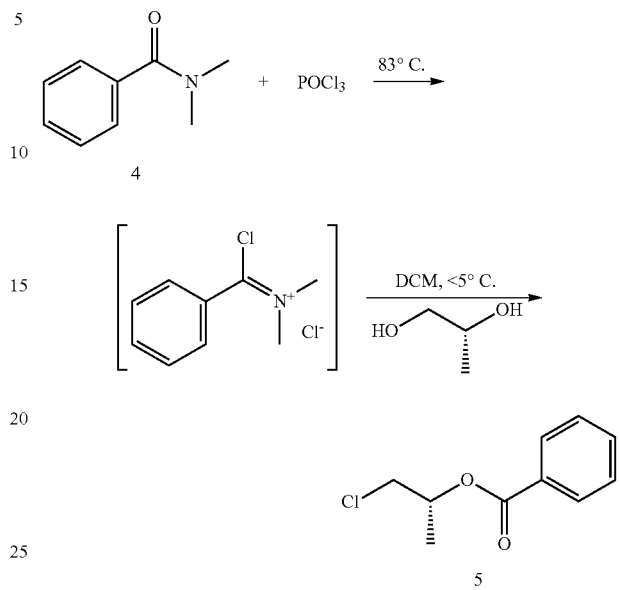

To a 10-liter jacketed pilot plant reaction vessel equipped with an overhead stirrer, a digital temperature monitor with a temperature probe, a reflux condenser, and a nitrogen line, 986 g (5 mol) of L-Dopa 2 was added followed by 2,183 g (10 mol) of di-tert-butyl dicarbonate anhydride ($Boc_2O$) and 1 L of methanol (MeOH) under a nitrogen atmosphere. The resulting suspension was warmed to 40° C. A tetrabutylammonium hydroxide solution (1,000 mL of a 1 M solution in methanol, 1 mol), water (36 mL, 2 mol), and methanol (100 mL) were added in five 1.136 L aliquots (a total of 5 mol of TBA-OH, 10 mL, $H_2O$ and 500 mL MeOH) over 30 minutes. After 5 hours, an additional 273 g (1.25 mol) of $Boc_2O$ anhydride was added. The reaction mixture was stirred at 40° C. for 21 hrs.

Possible traces of unreacted L-Dopa were filtered off under nitrogen by vacuum filtration into a 20 L rotary evaporator flask using a gas dispersion tube with a coarse, glass frit for the filtration. The filtrate was concentrated under vacuum to an oil. The oil was diluted under nitrogen with ethyl acetate (EtOAc) (16.5 L). The milky mixture was stirred at room temperature for 40 hrs. During this time the product precipitated out as a white to off-white solid. The resulting mixture was further cooled using an ice-bath for 1 h. The product was collected by centrifugation and washed with ethyl acetate (EtOAc) (500 mL). The resulting white solid was dried in a vacuum oven at 40° C. for 20 hrs to provide 2479.2 g (92.2% yield) of Boc-L-dopa tetrabutylammonium salt 3. $^1$H NMR (400 MHz, $CD_3CN$): δ 0.95 (t, J=7.2 Hz, 12H), 1.33 (m, 8H), 1.42 (s, 9H), 1.57 (m, 8H), 2.88 (m, 2H), 3.05 (m, 8H), 3.93 (m, 1H), 5.40 (d, J=6.4 Hz, 1H), 6.33 (dd, J=7.8, 1.6 Hz, 1H), 6.47 (d, J=8.0 Hz, 1H), 6.60 (d, J=2.0 Hz, 1H).

To a 10 liter mini pilot plant was added 3133 g (21.04 mol) of N,N-dimethylbenzamide 4 followed by 3,624 g (23.7 mol) of phosphorus oxychloride. The resulting suspension was stirred under nitrogen and slowly warmed. The suspension cleared as the reaction was warmed. When the temperature reached 40° C. an exotherm occurred which brought the temperature up to 83° C. over a few minutes. The reaction was stirred at 83° C.

The formation of the intermediate Vilsmeier salt was complete in 15 minutes at 85° C. as determined by $^1$H-NMR. The reaction was stirred an additional 1.5 hrs. The resulting clear, yellow solution was transferred to another 10 liter pilot plant and cooled to 0° C., and then diluted with two liters of dichloromethane (DCM). Two (2) kg (26.3 mole) of (R)-1,2-propanediol was slowly added to the reaction mixture over 2 hours while maintaining the temperature between 0° C. and 10° C.

Upon completion of the diol addition, the external cooling was removed and the reaction mixture was warmed to room temperature and stirred for 16 hours.

Two (2) L of the reaction mixture was added to 2 L of ice cold water with vigorous stirring to thoroughly mix the two phases. The phases were then separated and the process repeated with the remaining reaction mixture (total 5 times). The combined organic phases were washed with brine (500 mL), dried with anhydrous sodium sulfate ($Na_2SO_4$), and concentrated to yield 3,850 g of a dark-orange oil. The oil was dissolved in heptane (8 L) and the organic phase washed with water (2 L) followed by brine (3×500 mL). The product was dried over anhydrous sodium sulfate ($Na_2SO_4$) and concentrated to provide 3,590 g of crude (1R)-2-chloro-isopropyl benzoate 5 as a dark, yellow-orange oil. $^1$H NMR (400 MHz, $CDCl_3$): δ 1.47 (d, J=6.4 Hz, 3H), 3.71 (m, 2H), 5.35 (m, 1H), 7.42 (m, 2H), 7.54 (t, J=7.6 Hz, 1H), 8.06 (d, J=7.2 Hz, 2H).

Step 3: (2R)-2-Phenylcarbonyloxypropyl (2S)-3-(3,4-dihydroxyphenyl)-2-[(tert-butoxy)carbonylamino]propanoate (6)

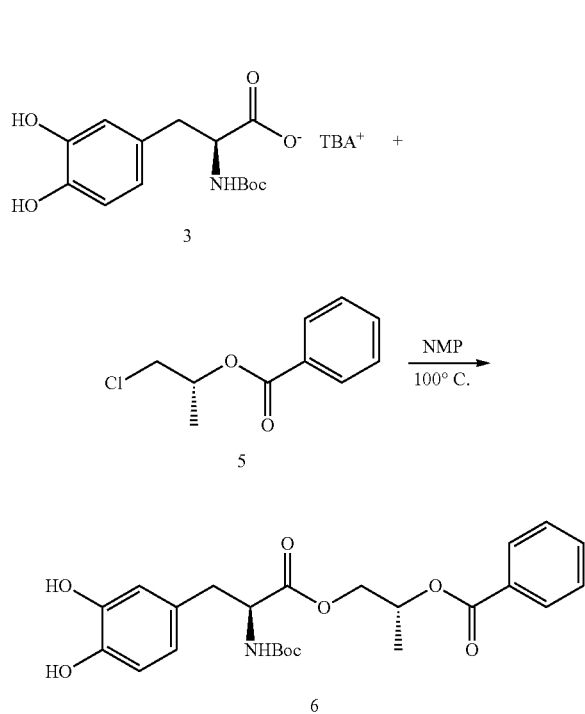

Boc-L-dopa tetrabutylammonium salt 3 (2000 g, 3.7 mol), N-methylpyrrolidone (3700 mL) and un-distilled chlorobenzoate (1R)-2-chloro-isopropyl benzoate 5 (1171 g, 5.91 mol) from Step 2 was added to a 10 L mini pilot plant. The resulting dark-green slurry was heated to 100° C. for 18 hours under nitrogen, which resulted in a clear, dark-yellow solution.

After 18 hrs a sample of the reaction mixture was diluted with methyl ten-butyl ether (MTBE) and extracted 3 times with water. This work-up efficiently extracted Boc-L-dopa tetrabutylammonium salt 3 into the water phase. The organic phase was evaporated and the progress of the reaction determined using $^1$H NMR in CDCl$_3$.

After cooling, the crude reaction mixture was divided in half and each part worked-up separately. The dark reaction mixture was transferred to a 22 L separatory funnel containing cold water (5 L). This mixture was then extracted with methyl tert-butyl ether (MTBE, 3 L). This sequence was repeated with the second half of the crude reaction mixture. The organic phases of both work-ups were combined and washed with water (2 L), brine (2 L), and dried over anhydrous sodium sulfate (Na$_2$SO$_4$). The solvent was evaporated and the resulting oil was triturated twice with heptane (2 L each) in a 45° C. water bath. The warm heptane phase was decanted. The resulting oil was further dried under vacuum for 2 hrs to provide 1,500 g of crude (2R)-2-phenylcarbonyloxypropyl (2S)-3-(3,4-dihydroxyphenyl)-2-[(tert-butoxy)carbonylamino]propanoate 6 as a dark oil. $^1$H NMR (CDCl$_3$) δ 1.4 (3 h, d), 1.45 (9 h, s), 2.95 (2H, d), 4.25 (1H, t), 4.2-4.6 (4H, m), 5.4 (1H, br s), 6.42 (2H, m), 6.7 (1H, d), 7.43 (2H, m), 7.6 (1H, m), 8.03 (2H, d); MS 482.19 (M+Na)$^+$, 458.14 (M-H)$^-$.

Step 4: (2R)-2-Phenylcarbonyloxypropyl (2S)-2-amino-3-(3,4-dihydroxyphenyl)propanoate, methanesulfonate (1)

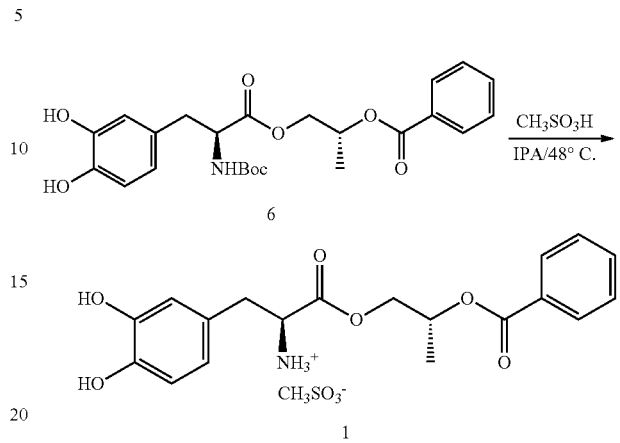

Crude (2R)-2-phenylcarbonyloxypropyl (2S)-3-(3,4-dihydroxyphenyl)-2-[(tert-butoxy)carbonylamino]propanoate 6 (1500 g) from Step 3 was dissolved in isopropanol (7,400 mL). Methanesulfonic acid (376 g, 3.9 mol) was added, which caused the temperature to rise to 49° C. The mixture was stirred for 16 hours at 45° C.

The reaction mixture was transferred to a 5-gallon plastic bucket and cooled to 5° C. for 7 hrs. The crystallized material was filtered using a basket centrifuge and washed with several aliquots of ethyl acetate (EtOAc) (ca. 4 L). The solid was dried under vacuum at 50° C. for 18 hrs to provide 723 g of (2R)-2-phenylcarbonyloxypropyl (2S)-2-amino-3-(3,4-dihydroxyphenyl)propanoate, methanesulfonate 1 as a white to off-white solid. Purity: 98.5% w/w; 97.6% AUC. M.p. 156-158° C. DSC: endotherm at 161.54° C. NMR (400 MHz, CD$_3$OD): δ 1.40 (d, J=6.4 Hz, 3H), 2.70 (s, 3H), 2.98 (dd, J=14.6, 7.8 Hz, 1H), 3.10 (dd, J=14.4, 5.6 Hz, 1H), 4.24 (dd, J=7.8, 5.8 Hz, 1H), 4.38 (dd, J=12, 0, 6.8 Hz, 1H), 4.52 (dd, J=311.8, 3.4 Hz, 1H), 5.40 (dq, J=6.4, 3.2 Hz, 1H), 6.52 (dd, J=7.8, 2.2 Hz, 1H), 6.69 (m, 2H), 7.48 (m, 2H), 7.60 (m, 1H), 8.01 (m, 2H).

Example 2

Alternate Step 3: (2R)-2-Phenylcarbonyloxypropyl (2S)-3-(3,4-dihydroxyphenyl)-2-[(tert-butoxy)carbonylamino]propanoate (6)

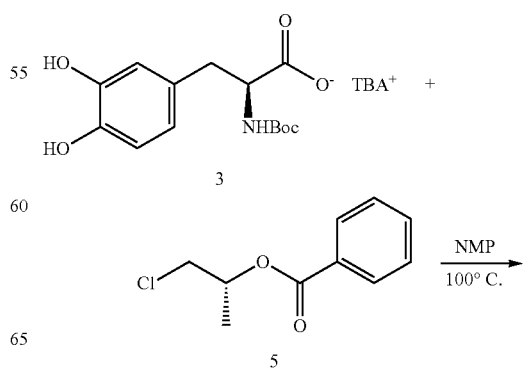

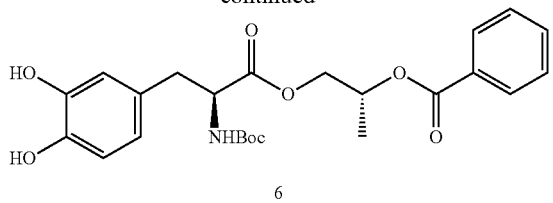

Boc-Dopa TBA salt 3 (50 g, 93 mmol), bicarbonate-washed (1R)-2-chloroisopropyl benzoate 5 (20 g, 100 mmol), and N-methylpyrrolidinone (NMP) (100 mL) were added to a 250 mL round bottom flask. The mixture was stirred under a nitrogen atmosphere and heated in an oil bath at 100° C. After ca. 72 hrs the reaction was cooled to room temperature, diluted with tert-butyl methylether (MTBE) (1 L), and washed twice with deionized water (2 L, then 1 L). The organic phase was separated, dried over anhydrous sodium sulfate ($Na_2SO_4$), filtered, and concentrated under reduced pressure to provide 35 g (76 mmol) of (2R)-2-phenylcarbonyloxypropyl (2S)-3-(3,4-dihydroxyphenyl)-2-[(tert-butoxy)carbonylamino]propanoate 6 as a tan, viscous oil.

Example 3

Alternate Step 4: (2R)-2-Phenylcarbonyloxypropyl (2S)-2-amino-3-(3,4-dihydroxyphenyl)propanoate, methanesulfonate (1)

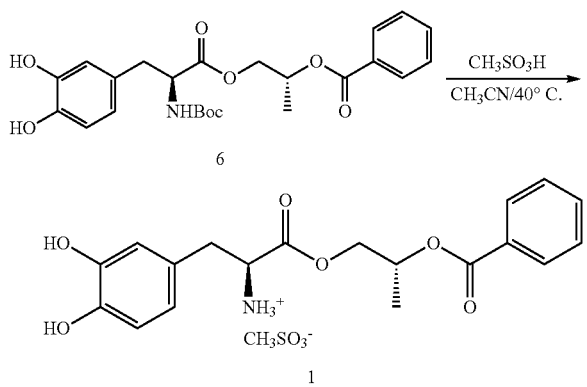

(2R)-2-Phenylcarbonyloxypropyl (2S)-3-(3,4-dihydroxyphenyl)-2-[(tert-butoxy)carbonylamino]propanoate 6 (35 g, 76 mmol) was dissolved in acetonitrile ($CH_3CN$) (150 mL). The mixture was stirred in a water bath at 40° C., followed by the addition of methanesulfonic acid (7.3 g, 4.93 mL). At 26° C. the reaction was seeded with 50 mg of (2R)-2-phenylcarbonyloxypropyl (2S)-2-amino-3-(3,4-dihydroxyphenyl)propanoate, methanesulfonate 1, followed by further cooling to 21° C. with formation of a thick slurry. The material was diluted with acetonitrile ($CH_3CN$) (150 mL) and cooled in a freezer at −20° C. for 16 hrs. The precipitate was then collected by filtration and washed with ethyl acetate (EtOAc) (500 mL). The off-white solid (19.3 g, 42 mmol) was dried under vacuum to provide 19.3 g (42 mmol) of (2R)-2-phenylcarbonyloxypropyl (2S)-2-amino-3-(3,4-dihydroxyphenyl)propanoate, methanesulfonate 1. $^1H$ NMR (DMSO-$d_6$) δ 1.30 (3 h, d), 2.29 (3H, s), 2.90 (2H, d), 4.25 (1H, t), 4.31 (1H, dd), 4.39 (1H, dd), 5.25 (1H, m), 6.41 (1H, dd), 6.57 (1H, d), 6.59 (1H, d), 7.52 (2H, m), 7.63 (1H, m), 7.93 (2H, m), 8.26 (3H, br s), 8.85 (1H, s), 8.89 (1H, s); mp 163-164° C. Purity (HPLC): 96.1 w/w % purity, and 95.0% purity by AUC.

Example 4

Recrystallization of (2R)-2-Phenylcarbonyloxypropyl (2S)-2-amino-3-(3,4-dihydroxyphenyl)propanoate, methanesulfonate (1)

(2R)-2-Phenylcarbonyloxypropyl (2S)-2-amino-3-(3,4-dihydroxyphenyl)propanoate, methanesulfonate 1 (19.3 g, 42 mmol) was suspended in acetonitrile ($CH_3CN$) (400 mL) and heated in a water bath at 80° C. Deionized water (4 mL) was then added causing most of the material to dissolve. The solution was filtered through a sintered glass funnel to remove undissolved solids. The solution was stirred and slowly cooled at a rate of 15° C./hour. At about 60° C. the solution began to crystallize. When the temperature reached 21° C. the solid was collected by filtration and washed with acetonitrile ($CH_3CN$) (100 mL) and tert-butyl methyl ether (MTBE) (100 mL). The solid was then dried under vacuum for 24 hrs to provide 14.7 g (32.3 mmol) of crystalline (2R)-2-phenylcarbonyloxypropyl (2S)-2-amino-3-(3,4-dihydroxyphenyl)propanoate, methanesulfonate 1 as an off-white solid.

Example 5

Synthesis of (2R)-2-Phenylcarbonyloxypropyl (2S)-2-amino-3-(3,4-dihydroxyphenyl)propanoate, Methanesulfonate (1)

Step 1: Boc-L-Dopa tetrabutylammonium salt (3)

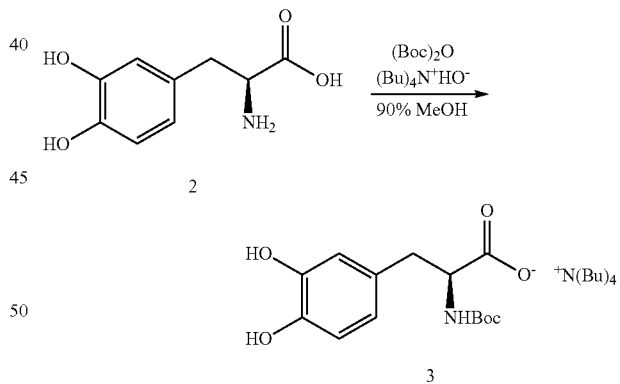

L-Dopa 2 (19 kg, 96 moles) and Boc-anhydride (42.2 kg, 193 moles) in 0.8 parts methanol (15 kg) were charged to a 380 L glass-lined reactor. The reactor was then charged with water (3.6 kg, 0.19 parts) in a 1 M tetrabutylammonium hydroxide methanol solution (80 kg, 4.21 parts) at 40° C., rinsing forwards with methanol (4 kg, 0.2 parts). The temperature of the mixture was adjusted to 45° C. to a maximum 50° C. and agitated for ca. 5 hours. Boc anhydride (5.3 kg, 24 moles, $Boc_2O$) was charged and rinsed forward with methanol (4 kg, 0.2 parts). The reaction was monitored until one of the two intermediates disappeared or became faint as determined by TLC and not more than 2% by HPLC. After filtration, the filtrate was concentrated to 4 volume parts (76 L) and the residue was co-evaporated with ethyl acetate (EtOAc) (95 kg, 15 parts) until 4 parts volume (76 L). After adjusting the temperature to 22° C. (19-25° C.), ethyl acetate (EtOAc) (287 kg, 15 parts) was charged and the resultant mixture was agitated at 22° C. (19-25° C.) for a minimum of 6 hours, cooled to 3° C. (0-6° C.) and agitated at 3° C. (0-6° C.) for a minimum of 10 hours. The product was filtered and washed with ethyl acetate (EtOAc) (19 kg, 1 part). The wet cake was slurry washed in ethyl acetate (EtOAc) (95 kg, 5 parts) at 22° C. (19-25° C.) for a minimum of 6 hrs. After filtration and washing with ethyl acetate (EtOAc) (19 kg, 1 part), the product, Boc-L-dopa tetrabutylammonium salt 3, was dried at a maximum temperature of 55° C. until LOD was max. 1%. The yield was 40.6 kg (78%) after correction for LOD and purity (minimum 97 A %).

Step 2: (1R)-2-Chloro-isopropyl Benzoate (5)

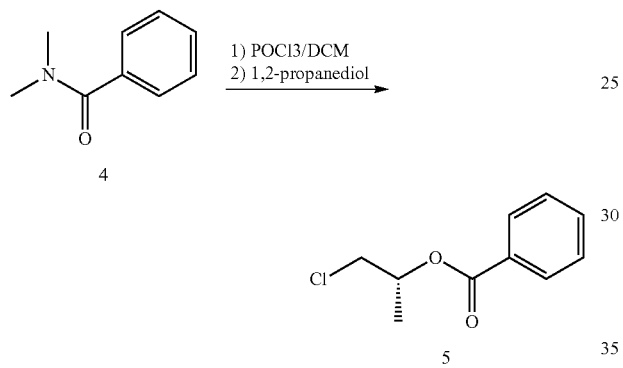

A 380 L glass lined reactor was conditioned with dichloromethane to remove moisture. Dimethylbenzamide 4 (30 kg, 201 moles) and dichloromethane (63 kg, 2.1 parts) were charged to the reactor and warmed to 40-45° C. Phosphorous oxychloride (34.5 kg, 225 mole, 1.15 parts) was charged over ca. 2 hrs while reflux was maintained using a metering pump. The line and pump were rinsed forward with dichloromethane (17 kg, 0.55 parts). The mixture was agitated under reflux for ca. 4 hrs. The temperature was adjusted to ca. 5° C. (R)-1,2-propanediol (19.2 kg, 252 moles, 0.64 parts) was diluted with dichloromethane (26 kg, 0.85 parts) in a drum. The solution was added to the reactor over ca. 5.4 hours (min 4 hrs), maintaining a temperature of 2° C. to 10° C. (target 5° C.). The pump and lines were rinsed forward with dichloromethane (3 kg, 0.1 parts). The temperature of the reactor was adjusted to 22° C. over ca. 80 min (minimum 60 min). The reactants were agitated for ca. 11 hrs. The reaction mixture was then transferred to a 760 L glass-lined reactor containing water (150 kg, 5 parts), maintaining a temperature from 19° C. to 40° C. until the exotherm ceased (ca. 1 hr). The temperature of the reactor was adjusted to 22° C. and the contents agitated for another ca. 1 hr. The phases were separated. The aqueous layer was back-extracted with dichloromethane (51 kg, 1.7 parts). The organic layers were combined and washed with an aqueous sodium bicarbonate solution (water 110 kg, 3.65 parts and sodium bicarbonate 5.7 kg, 0.19 parts). The pH of the organic layer (pH≥7) and aqueous layer (pH≥9) were determined, and then the phases were separated. Sodium sulfate (9 kg, 0.3 parts) was added to the organic layer and the mixture agitated at 22° C. for ca. 60 min. The slurry was filtered to remove sodium sulfate (Na$_2$SO$_4$) (125 L pressure Nutsche) to provide a final stock solution (269 kg, TDS 11.3%, HPLC 91.3 A %). The reactor and filtrate were rinsed forward with dichloromethane (30 kg, 1 part) to provide a rinse solution containing (1R)-2-chloro-isopropyl benzoate 5 (25.5 kg, TDS 1.5%, HPLC 91.7 A %) (yield 70.9%).

Step 3: (2R)-2-phenylcarbonyloxypropyl (2S)-3-(3,4-dihydroxyphenyl)-2-[(tert-butoxy)carbonylamino]propanoate (6)

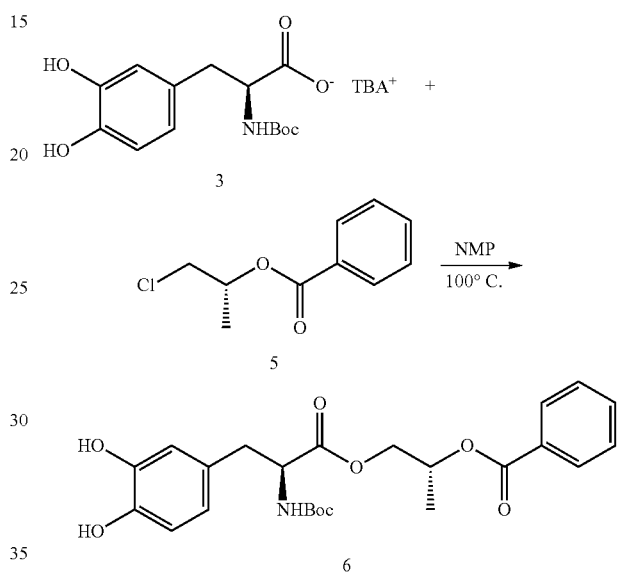

A 380 L glass lined reactor was conditioned with dichloromethane to remove moisture. The (1R)-2-chloro-isopropyl benzoate 5 stock solution from Step 2 (205 kg, TDS 11.3%, 21.3 kg, 107.2 moles, 1.5 eq) was charged to the reactor and concentrated until distillation stopped, at a maximum W/G temperature of 50° C. Vacuum was then applied at maximum W/G temperature of 40° C., and concentration was continued for ca. 1 hour. A dichloromethane content of 1.6% was achieved.

1-Methyl-2-pyrrolidone (NMP) (77.7 kg, 2.0 parts) was charged to the reactor and the temperature was adjusted to 22° C. Boc-Dopa TBA 3 (38.7 kg, 1.0 part, 71.83 moles) was charged to the reactor via a hand hole, followed by potassium phosphate, dibasic (12.4 kg, 71.19 moles, 0.32 parts, 1 eq). The temperature was adjusted to 100° C. (97-103° C.), and reacted until the reaction was complete as determined by HPLC (20-36 hr). After the reaction was complete, the temperature was adjusted to 22° C. (19-25° C.) and the solids filtered off (pressure Nutsche). The reaction and filter were forward rinsed with 1-methyl-2-pyrrolidone (NMP) (39.2 kg, 1.0 part). The filtrate and rinse were transferred to a 1,900 L glass-lined reactor and the organics washed three times to partially remove un-reacted starting material. Heptane (126 kg, 3.25 parts) was charged to the reactor, followed by tetrahydrofuran (9.7 kg, 0.25 parts), and the contents were agitated at 22° C. for ca. 1 hour. The layers were allowed to separate for ca. 60 minutes.

The lower organic layer containing 1-methyl-2-pyrrolidone (NMP) and (2R)-2-phenylcarbonyloxypropyl (2S)-3-(3,4-dihydroxyphenyl)-2-[(tert-butoxy)carbonylamino]propanoate 6 was transferred to a 380 L glass-lined reactor. The remaining organics in the 1,900 L reactor were jogged for ca. 10 seconds, every 15 minutes for ca. 60 minutes, to loosen any product containing organics from the reactor walls, which were then drained to the 380 L reactor. The organics were returned to the 1,900 L reactor and washed twice with THF/heptane. After the final THF/heptane wash, the organic layer was returned to the 1900 L reactor. Methyl tert-butyl ether (MTBE) (39 kg, 1 part) was charged to the 380 L reactor and agitated. Water (39 kg, 1 part) was added to the 380 L reactor and agitated for 15 minutes. The 380 L reactor, the pump, and the lines were rinsed forward to the 1,900 L reactor. Methyl tert-butyl ether (MTBE) (116 kg, 3 parts) was added to the 1,900 L reactor, followed by water (368 kg, 9.5 parts) at a maximum temperature of 30° C. The addition of water was exothermic. The temperature was adjusted to 22° C. (19-25° C.) and the reactants moderately agitated for ca. 1 hour. Agitation was stopped and the layers allowed to separate for ca. 60 minutes.

The lower aqueous layer was transferred to 200 L polyethylene drums using a 30 L separatory funnel and the upper organic layer was transferred to the 380 L reactor. The aqueous layer was returned to the 1900 L reactor and methyl tert-butyl ether (MTBE) (77 kg, 2 parts) was added. The temperature was adjusted to 22° C. (19-25° C.) and the mixture moderately agitated for ca. 1 h. Agitation was stopped, and the layers allowed to separate for ca. 60 minutes. The lower aqueous layer was discharged using a 30 L separatory funnel. The organic product was transferred to the 1,900 L reactor and combined with the organic methyl tert-butyl ether (MTBE) layer in the 1,900 L reactor. The 380 L reactor and the pump lines were rinsed forward with ca. 20 kg methyl tert-butyl ether (MTBE) to the 1,900 L reactor. A solution of sodium bicarbonate (21.3 kg, 0.55 parts) in water (271 kg, 7.0 parts) was added to the organic layer while maintaining the temperature of the reactor at less than 30° C. The temperature was adjusted to 22° C. (19-25° C.) and moderately agitated for ca. 1 hour.

Agitation was stopped, and the layers were allowed to separate for ca. 60 minutes. The target pH parameter, for the organic layer was pH≥7, and the target for the aqueous layer was pH≥9. The aqueous layer was drained to drums until the emulsion became visible. Diatomaceous earth (10 kg) was added to the reactor and the mixture agitated for ca. 15-30 minutes. The mixture was filtered through a pressure Nutsche and the filtrate drained to clean polyethylene drums. The filtrate was then transferred to the 1900 L reactor. Water (77.4 kg, 2 parts) was added to the reactor and moderately agitated for ca. 1 hour. Agitation was stopped and the layers allowed to separate for ca. 60 minutes. The aqueous layer was then drained into polyethylene drums. Sodium sulfate (Na$_2$SO$_4$) (39.2 kg, 1 part) was added and the mixture agitated at 22° C. for ca. 60 min. The slurry was filtered to remove sodium sulfate (Na$_2$SO$_4$) using a 125 L pressure Nutsche to provide a solution containing (2R)-2-phenylcarbonyloxypropyl (2S)-3-(3,4-dihydroxyphenyl)-2-[(tert-butoxy)carbonylamino]propanoate 6 (214 kg methyl tert-butyl ether (MTBE) stock solution, TDS 12.4%, HPLC 51.4 A %, 13.5 kg (2R)-2-phenylcarbonyloxypropyl (2S)-3-(3,4-dihydroxyphenyl)-2-[(tert-butoxy)carbonylamino]propanoate 6). The reactor, pump lines, and filter were rinsed forward with MTBE (50 kg, 2 parts) and drummed off separately (98.4 kg, TDS 0.83%%, HPLC 47.9 A %, 0.39 kg, a total of 13.9 kg (2R)-2-phenylcarbonyloxypropyl (2S)-3-(3,4-dihydroxyphenyl)-2-[(tert-butoxy)carbonylamino]propanoate 6, 42.4% yield. 35-65% expected).

Step 4: (2R)-2-phenylcarbonyloxypropyl (2S)-2-amino-3-(3,4-dihydroxyphenyl)propanoate, methanesulfonate (1)

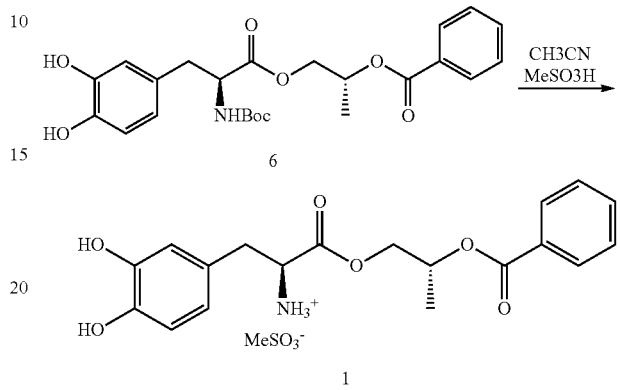

The solution of (2R)-2-phenylcarbonyloxypropyl (2S)-3-(3,4-dihydroxyphenyl)-2-[(tert-butoxy)carbonylamino]propanoate 6 from Step 3 was added to a 570 L glass-lined reactor and rinsed with methyl tert-butyl ether (MTBE) (312.4 kg, 13.9 kg). The contents were concentrated under vacuum at a maximum W/G temperature of 40° C. until distillation stopped. Acetonitrile (CH$_3$CN) (116 kg, 3.0 parts) was charged to the reactor and the vacuum distillation repeated until distillation ended. Additional acetonitrile (CH$_3$CN) (112 kg, 2.9 parts) was charged to the reactor and the temperature was adjusted to 40° C. (39-41° C.). Methanesulfonic acid (MeSO$_3$H) (6.97 kg, 0.18 parts) was charged to the reactor while maintaining the temperature at 40° C. (35-45° C.). The pump and lines were rinsed forward with acetonitrile (CH$_3$CN) (3.9 kg, 0.1 part). The reaction was complete after two hrs (2-6 hrs expected) at 40° C. (35-45° C.) as determined by high pressure liquid chromatography (HPLC). The temperature of the mixture was adjusted to 22° C. (19-25° C.) and agitated for 32 hrs. The crude product was collected by centrifugation, the reactor, lines, and filter cake rinsed forward with acetonitrile (CH$_3$CN) (38.7 kg, 1 part) and spun as dry as possible to provide a wet filter cake (10.9 kg). A portion of the wet filter cake (8.0 kg) was transferred to a 570 L glass-lined reactor. Acetonitrile (CH$_3$CN) (278 kg, 10 parts) was charged to the reactor, the contents agitated, and the temperature adjusted to reflux (80-82° C.). Water (2.8 kg, 0.1 parts) was charged to the reactor, maintaining the temperature at 80-82° C. The suspension became a clear solution. The mixture was agitated at 80-82° C. for ca. 30 minutes. The solution was then cooled over 6 hrs to 22° C. (19-25° C.) with a slurry forming at 60° C. The slurry was held at 22° C. (19-25° C.) for an additional 2 hrs. The product, (2R)-2-phenylcarbonyloxypropyl (2S)-2-amino-3-(3,4-dihydroxyphenyl)propanoate, methanesulfonate 1, was collected by centrifugation and the reactor, lines, and filter cake were rinsed with 3 portions of methyl tert-butyl ether (MTBE) (30 kg each) and spun dry. The product was dried at a maximum temperature of 55° C. until LOD was ≤0.5% and acetonitrile is ≤400 ppm as determined by gas chromatography (GC) to provide 5.4 kg of (2R)-2-phenylcarbonyloxypropyl (2S)-2-amino-3-(3,4-dihydroxyphenyl)propanoate, methanesulfonate 1.

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of synthesizing (2R)-2-phenylcarbonyloxypropyl (2S)-2-amino-3-(3,4-dihydroxyphenyl)propanoate salt comprising:
reacting (2S)-2-amino-3-(3,4-dihydroxyphenyl)propanoic acid with di-tert-butyl dicarbonate and tetrabutylammonium hydroxide in a mixture of alcohol and from 0%-b.v. to 4 b.v. water at a temperature from 20° C. to 60° C. in an inert atmosphere, to provide 3-(3,4-dihydroxyphenyl)-(2S)-[(tert-butoxy)carbonylamino] propanoate tetrabutylammonium salt; and
reacting the 3-(3,4-dihydroxyphenyl)-(2S)-[(tert-butoxy)carbonylamino]propanoate tetrabutylammonium salt with (1R)-2-chloro-isopropyl benzoate in N-methyl-2-pyrrolidone at a temperature from 50° C. to 120° C. to provide (2R)-2-phenylcarbonyloxypropyl(2S)-3-(3,4-dihydroxyphenyl)-2-[(tert-butoxy)carbonylamino] propanoate.

2. The method of claim 1, wherein the reacting (2S)-2-amino-3-(3,4-dihydroxyphenyl)propanoic acid with di-tert-butyl dicarbonate and tetrabutylammonium hydroxide was carried out at a temperature from 20° C. to 60° C.

3. The method of claim 1, wherein the alcohol is selected from methanol, ethanol, isopropanol, and a mixture of any of the foregoing.

4. The method of claim 1, wherein,
the alcohol is methanol; and
the purity of the (2R)-2-phenylcarbonyloxypropyl (2S)-2-amino-3-(3,4-dihydroxyphenyl)propanoate, methanesulfonate is greater than 97%.

5. The method of claim 1, comprising, after reacting the 3-(3,4-dihydroxyphenyl)-(2S)-[(tert-butoxy)carbonylamino]propanoate tetrabutylammonium salt with (1R)-2-chloro-isopropyl benzoate:
reacting (2R)-2-phenylcarbonyloxypropyl (2S)-3-(3,4-dihydroxyphenyl)-2-[(tert-butoxy)carbonylamino]propanoate with methanesulfonic acid in a solvent to provide (2R)-2-phenylcarbonyloxypropyl (2S)-2-amino-3-(3,4-dihydroxyphenyl)propanoate, methanesulfonate
wherein the purity of the (2R)-2-phenylcarbonyloxypropyl (2S)-2-amino-3-(3,4-dihydroxyphenyl)propanoate, methanesulfonate prior to recrystallization is greater than 95%.

6. The method of claim 5, wherein reacting (2R)-2-phenylcarbonyloxypropyl (2S)-3-(3,4-dihydroxyphenyl)-2-[(tert-butoxy)carbonylamino]propanoate with methanesulfonic acid to provide (2R)-2-phenylcarbonyloxypropyl (2S)-2-amino-3-(3,4-dihydroxyphenyl)propanoate,
methanesulfonate is carried out at a temperature ranging from about 30° C. to about 50° C.

7. The method of claim 1, comprising cooling the solvent to form crystalline (2R)-2-phenylcarbonyloxypropyl (2S)-2-amino-3-(3,4-dihydroxyphenyl)propanoate, methanesulfonate.

8. The method of claim 7, comprising seeding the cooled solvent with crystalline (2R)-2-phenylcarbonyloxypropyl (2S)-2-amino-3-(3,4-dihydroxyphenyl)propanoate, methanesulfonate.

9. The method of claim 7, comprising recrystallizing (2R)-2-phenylcarbonyloxypropyl (2S)-2-amino-3-(3,4-dihydroxyphenyl)propanoate, methanesulfonate.

10. The method of claim 9, wherein recrystallizing (2R)-2-phenylcarbonyloxypropyl (2S)-2-amino-3-(3,4-dihydroxyphenyl)propanoate, methanesulfonate comprises:
dissolving (2R)-2-phenylcarbonyloxypropyl (2S)-2-amino-3-(3,4-dihydroxyphenyl)propanoate, methanesulfonate in a solvent; and
cooling the solvent to form crystalline (2R)-2-phenylcarbonyloxypropyl (2S)-2-amino-3-(3,4-dihydroxyphenyl)propanoate, methanesulfonate.

* * * * *